(12) United States Patent
Nishimura et al.

(10) Patent No.: US 9,416,081 B2
(45) Date of Patent: Aug. 16, 2016

(54) METHOD FOR PRODUCING ALDEHYDE

(71) Applicant: Kao Corporation, Tokyo (JP)

(72) Inventors: Ryo Nishimura, Wakayama (JP); Jun Kono, Wakayama (JP); Tsubasa Arai, Wakayama (JP)

(73) Assignee: KAO CORPORATION, Tokyo (JP)

( * ) Notice: Subject to any disclaimer, the term of this patent is extended or adjusted under 35 U.S.C. 154(b) by 0 days.

(21) Appl. No.: 14/653,035

(22) PCT Filed: Dec. 2, 2013

(86) PCT No.: PCT/JP2013/082381
§ 371 (c)(1),
(2) Date: Jun. 17, 2015

(87) PCT Pub. No.: WO2014/097873
PCT Pub. Date: Jun. 26, 2014

(65) Prior Publication Data
US 2015/0344391 A1     Dec. 3, 2015

(30) Foreign Application Priority Data
Dec. 18, 2012 (JP) ................................ 2012-275985

(51) Int. Cl.
    *C07C 45/29*         (2006.01)
    *B01J 23/745*      (2006.01)
    *B01J 37/03*        (2006.01)
    *B01J 37/18*        (2006.01)
    *B01J 37/00*        (2006.01)
    *B01J 37/02*        (2006.01)
    *B01J 23/72*        (2006.01)
    *B01J 23/80*        (2006.01)

(52) U.S. Cl.
CPC ................. *C07C 45/29* (2013.01); *B01J 23/72* (2013.01); *B01J 23/745* (2013.01); *B01J 23/80* (2013.01); *B01J 37/0009* (2013.01); *B01J 37/0215* (2013.01); *B01J 37/031* (2013.01); *B01J 37/18* (2013.01); *B01J 2523/00* (2013.01)

(58) Field of Classification Search
CPC .................................. C07C 45/29; B01J 23/00
USPC ........................................................... 568/485
See application file for complete search history.

(56) References Cited

U.S. PATENT DOCUMENTS

| 4,072,717 A | 2/1978 | Halbritter et al. |
| 2010/0010268 A1 | 1/2010 | Shirasawa et al. |

FOREIGN PATENT DOCUMENTS

| EP | 2 868 646 A1 | 5/2015 |
| JP | 48-029742 A | 4/1973 |
| JP | 51-054507 A | 5/1976 |
| JP | 5-070739 A | 3/1993 |
| JP | 5-168928 A | 7/1993 |
| JP | 2008-184452 A | 8/2008 |
| JP | 2010-099635 A | 5/2010 |
| JP | 2010-227925 A | 10/2010 |
| JP | 2012-126676 A | 7/2012 |
| JP | 2014-009167 A | 1/2014 |

OTHER PUBLICATIONS

International Search Report issued in PCT/JP2013/082381, mailed on Feb. 25, 2014.

*Primary Examiner* — Sikarl Witherspoon

(74) *Attorney, Agent, or Firm* — Birch, Stewart, Kolasch & Birch, LLP

(57) ABSTRACT

Provided is a method for producing an aldehyde that provides a target aldehyde at a high conversion rate over an extended period of time. It is a method for producing an aldehyde comprising bringing a raw material gas containing a primary alcohol having 4 to 18 carbon atoms and water into contact with a dehydrogenation catalyst containing copper and iron so as to dehydrogenate the alcohol contained in the raw material gas, thereby obtaining an aldehyde, wherein the raw material gas has a water partial pressure of 0.2 kPa to 99 kPa.

20 Claims, 1 Drawing Sheet

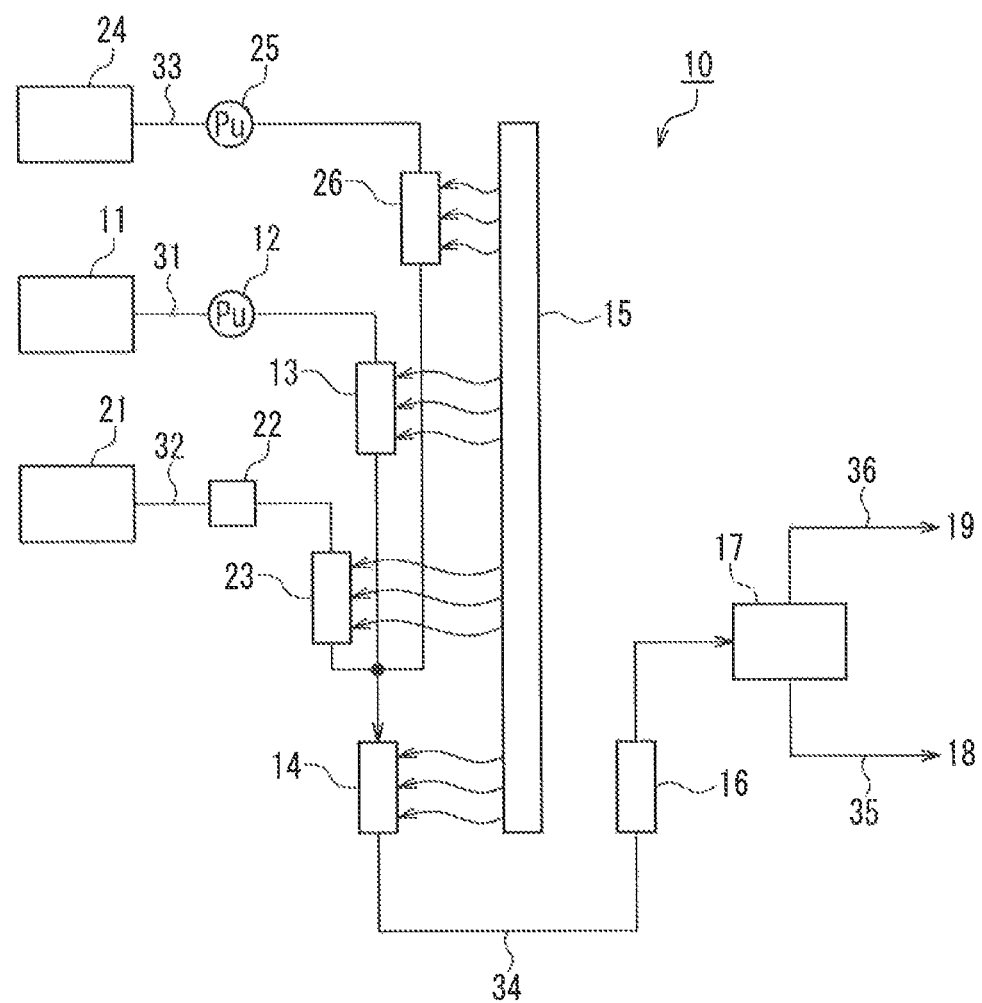

METHOD FOR PRODUCING ALDEHYDE

TECHNICAL FIELD

The present invention relates to a method for producing an aldehyde.

BACKGROUND ART

An aliphatic aldehyde having a specific molecular weight is useful as a fragrance material and further is also used as a raw material for derivatives having different fragrance notes.

Examples of conventionally known methods for producing an aldehyde include dehydrogenation or oxidation using alcohol as a raw material. Among them, since dehydrogenation is an endothermic reaction while oxidation is an exothermic reaction, dehydrogenation is frequently used as a method for producing an aldehyde due to the easy thermal control thereof. Moreover, catalysts for dehydrogenation also have been studied.

For example, Patent Document 1 discloses a method of producing an aldehyde by dehydrogenation of gaseous alcohol in the presence of a solid catalyst with low surface acidity.

Patent Document 2 discloses a method for producing a formaldehyde, which is characterized in that gaseous methanol is subjected to oxidative dehydrogenation in the presence of a silver catalyst, a specific amount of water vapor, and an exhaust gas with a specific composition that was produced in a formaldehyde production, wherein the reaction is initiated at a low methanol load and a low temperature.

Patent Document 3 discloses a method of producing an aldehyde by dehydrogenation of an alcohol in the presence of a solid catalyst carrying copper, iron, and aluminum at an atomic ratio in a specific range.

PRIOR ART DOCUMENTS

Patent Documents

[Patent Document 1] JP 2010-99635 A
[Patent Document 2] JP 51(1976)-54507 A
[Patent Document 3] JP 5(1993)-168928 A

DISCLOSURE OF INVENTION

Problem to be Solved by the Invention

In producing an aldehyde by dehydrogenation of a primary alcohol through a gas phase reaction in the presence of a solid catalyst, the aldehyde produced therein is retained at an active site on the catalyst for a long period of time and thereby side reactions such as oligomerization between the primary alcohol and the aldehyde occur. Thus, components that tend not to volatilize are accumulated on the catalyst and thereby the catalyst is inactivated, which results in a decrease in the conversion rate of the primary alcohol at an early stage. This has been a problem.

Patent Document 1 describes that due to the decrease in the surface acidity of a catalyst, addition reactions between aldehydes produced by dehydrogenation of an alcohol or between an aldehyde and a component contained in the reaction system are suppressed and thereby the selectivity of the aldehyde is improved. However, it neither describes nor suggests the improvements in the conversion rate of the primary alcohol used as a raw material and the durability of the catalyst. Furthermore, Patent Document 1 refers only to ethanol having 2 carbon atoms.

Patent Document 2 suggests that when methanol is oxidized in the presence of exhaust gas containing water vapor, the production of soot is suppressed. However, both the patent documents neither describe nor suggest the suppression of oligomerization of an aldehyde in the dehydrogenation of an alcohol having at least 4 carbon atoms and the improvements in the catalyst durability and the conversion rate of the primary alcohol by the suppression of the oligomerization.

Furthermore, Patent Document 3 discloses dehydrogenation of a primary alcohol having 8 to 12 carbon atoms in the presence of a copper-iron-aluminum catalyst. However, it does not specifically disclose the method of improving the catalyst durability at all.

Therefore, the present invention is intended to provide a method for producing an aldehyde, in which a target aldehyde can be obtained at a high conversion rate over an extended period of time.

Means for Solving Problem

The present inventors thought that in order to obtain a target aldehyde at a high conversion rate over an extended period of time, it is effective to prevent by production of high molecular weight components that accumulate on the active sites of a catalyst to inactivate the catalyst and that tend not to volatilize, and they examined it extensively. As a result, they found that when a primary alcohol having 4 to 18 carbon atoms was mixed with water, the partial pressure of the water contained in the mixture was set in a specific range, and the mixture was brought into contact with a dehydrogenation catalyst containing copper and iron so as to dehydrogenate, the production of a compound to be a precursor of various high molecular weight components to be produced was suppressed. The reason for this is not clear but it can be considered as follows. It is considered that the high molecular weight components are produced by the dehydration of an aldehyde. However, it is considered that in the case of using the partial pressure of the water according to the present application in the above-mentioned mixture, the high molecular weight components return to the aldehyde due to a reverse reaction. Based on such findings, the present inventors completed the present invention.

That is, the present invention is a method for producing an aldehyde comprising bringing a raw material gas containing a primary alcohol having 4 to 18 carbon atoms and water into contact with a dehydrogenation catalyst containing copper and iron so as to dehydrogenate the alcohol contained in the raw material gas, thereby obtaining an aldehyde, wherein the raw material gas has a water partial pressure of 0.2 kPa to 99 kPa.

Effects of the Invention

The present invention can provide a method for producing an aldehyde in which a target aldehyde can be obtained at a high conversion rate over an extended period of time.

BRIEF DESCRIPTION OF DRAWINGS

FIG. 1 is a block diagram showing a first apparatus configuration.

DESCRIPTION OF THE INVENTION

The method for producing the aldehyde of the present invention is a method for producing an aldehyde comprising bringing a raw material gas containing a primary alcohol having 4 to 18 carbon atoms and water into contact with a dehydrogenation catalyst containing copper and iron so as to dehydrogenate the alcohol contained in the raw material gas, thereby obtaining an aldehyde, wherein the raw material gas has a water partial pressure of 0.2 kPa to 99 kPa.

In the present invention, the raw material gas contains a primary alcohol having 4 to 18 carbon atoms and water. In the raw material gas, the water partial pressure is 0.2 kPa to 99 kPa. The partial pressure of the water in the raw material gas is at least 0.2 kPa, preferably at least 1 kPa, more preferably at least 10 kPa, and further preferably at least 40 kPa in terms of suppressing the inactivation of the catalyst. Furthermore, in terms of obtaining an aldehyde efficiently and suppressing the production of byproducts, the partial pressure of the water is not more than 99 kPa, preferably not more than 90 kPa, more preferably not more than 80 kPa, and further preferably not more than 60 kPa. The partial pressure of the water in the raw material gas is 0.2 kPa to 99 kPa, preferably 1 kPa to 90 kPa, more preferably 10 kPa to 80 kPa, further preferably 40 kPa to 80 kPa, and still further preferably 40 kPa to 60 kPa. The water concentration in the reaction raw material gas is preferably at least 0.05 mol/m$^3$, more preferably at least 0.11 mol/m$^3$, and further preferably at least 0.40 mol/m$^3$ in terms of suppressing the inactivation of the catalyst. Moreover, in terms of obtaining an aldehyde efficiently and suppressing the production of byproducts, the water concentration in the reaction raw material gas is preferably not more than 23 mol/m$^3$, more preferably not more than 20 mol/m$^3$, further preferably not more than 18 mol/m$^3$, and still further preferably not more than 14 mol/m$^3$.

In the present invention, the partial pressure of the primary alcohol in the raw material gas is preferably not more than 50 kPa, more preferably not more than 30 kPa, and further preferably not more than 20 kPa in terms of gasifying the primary alcohol. Furthermore, in terms of obtaining an aldehyde efficiently, the partial pressure of the primary alcohol, which has been vaporized, in the raw material gas is preferably at least 1 kPa, more preferably at least 5 kPa. Moreover, the partial pressure of the primary alcohol in the raw material gas is preferably 1 kPa to 50 kPa, more preferably 5 kPa to 30 kPa, and further preferably 5 kPa to 20 kPa.

The temperature for the dehydrogenation in which the raw material gas is brought into contact with the dehydrogenation catalyst is preferably at least 200° C., more preferably at least 220° C., and further preferably at least 240° C. in terms of the alcohol conversion rate. Furthermore, the temperature for the dehydrogenation is preferably not more than 300° C., more preferably not more than 270° C. in terms of the energy efficiency. Moreover, the temperature for the dehydrogenation is preferably 200° C. to 300° C., more preferably 220° C. to 270° C., and further preferably 240° C. to 270° C.

The pressure for the dehydrogenation in which the raw material gas is brought into contact with the dehydrogenation catalyst is preferably not more than 102 kPa, more preferably 10 kPa to 102 kPa in absolute pressure in terms of vaporizing the product.

With respect to the pressure for the dehydrogenation, the pressure for the dehydrogenation in the case where the primary alcohol of the raw material has not more than 10 carbon atoms is more preferably at least 80 kPa, further preferably at least 90 kPa in absolute pressure. Furthermore, the pressure for the dehydrogenation in the case where the primary alcohol of the raw material has not more than 10 carbon atoms is preferably not more than 102 kPa. Moreover, the pressure for the dehydrogenation in the case where the primary alcohol of the raw material has not more than 10 carbon atoms is preferably 80 kPa to 102 kPa, more preferably 90 kPa to 102 kPa. On the other hand, the pressure for the dehydrogenation in the case where the primary alcohol of the raw material has at least 11 carbon atoms is more preferably at least 10 kPa, further preferably at least 13 kPa in absolute pressure. Furthermore, the pressure for the dehydrogenation in the case where the primary alcohol of the raw material has at least 11 carbon atoms is preferably not more than 102 kPa. Moreover, the pressure for the dehydrogenation in the case where the primary alcohol of the raw material has at least 11 carbon atoms is preferably 10 kPa to 102 kPa, more preferably 13 kPa to 102 kPa.

In the present invention, the raw material gas contains the primary alcohol and water. The primary alcohol can be vaporized beforehand by a means such as heating, decompression, etc. Preferably, the vaporization is carried out by heating the primary alcohol. In terms of vaporizing the primary alcohol, it is heated to preferably at least 200° C., more preferably at least 220° C., and further preferably at least 230° C. Furthermore, in terms of the thermal history with respect to the primary alcohol, it is heated to preferably not more than 500° C., more preferably not more than 400° C., and further preferably not more than 300° C.

The period of time for heating the primary alcohol is preferably at least 10 seconds, more preferably at least 5 minutes in terms of vaporizing the primary alcohol. Furthermore, in terms of the thermal history with respect to the primary alcohol, the heating time is preferably not more than 2 hours, more preferably not more than 1 hour, and further preferably not more than 30 minutes.

Examples of the container in which the primary alcohol is heated include a storage tank in which a stainless steel piping provided with a heat source, a stainless steel pipe for circulating a heated medium, etc. are placed.

Preferably, the water contained in the raw material gas is vaporized beforehand by a means such as heating, decompression, etc. In terms of preventing the condensation of the primary alcohol when the water is mixed with the primary alcohol that has been vaporized, it is preferable that the water be vaporized beforehand by heating.

In the present invention, the raw material gas containing a primary alcohol and water can be prepared by a method in which the primary alcohol and water each are vaporized independently and then are mixed together or a method in which they are mixed together before being vaporized. The method is not particularly limited as long as it does not adversely affect the reaction. However, in terms of mixing the primary alcohol and water uniformly, it is preferable that the raw material gas containing a primary alcohol and water be prepared by the method in which the primary alcohol and water are vaporized and then are mixed together.

In the present invention, the raw material gas may further contain an inert gas. In the present invention, the raw material gas further containing an inert gas can be prepared by a method in which a mixed gas of a primary alcohol and water that have been vaporized is mixed with an inert gas, a method in which a primary alcohol that has been vaporized is mixed with an inert gas, a method in which water that has been vaporized is mixed with an inert gas, a method in which a liquid mixture of a primary alcohol and water that have not been vaporized is mixed with an inert gas, a method in which a primary alcohol that has not been vaporized is mixed with an inert gas, a method in which water that has not been vaporized is mixed with an inert gas, etc. The method is not particularly limited as long as it does not adversely affect the reaction. However, in terms of mixing them uniformly, it is preferable that the raw material gas further containing an inert gas be prepared by a method in which a mixed gas of a primary alcohol and water that have been vaporized is mixed with an inert gas, a method in which a primary alcohol that has been vaporized is mixed with an inert gas, or a method in which water that has been vaporized is mixed with an inert gas.

In the present invention, examples of the method for bringing a raw material gas into contact with a dehydrogenation catalyst include a method of passing the raw material gas, preferably continuously, through a reactor charged with a catalyst, thereby dehydrogenating in the reactor.

Examples of the reactor include a tubular flow reactor, a vessel-type reactor, etc. In terms of discharging the aldehyde produced therein from the reactor quickly, a tubular flow reactor is preferred.

In the case of using a tubular flow reactor, it is preferable that the reaction is proceeded continuously or batch-wise by a single flow or circulation feed by a flow system in which a product is collected continuously while a raw material gas is fed to a dehydrogenation catalyst contained in a tube. Also, a method for supplying the raw material gas can be either upflow or downflow. Also, when a vessel-type reactor is used, the reaction is proceeded continuously or batch-wise with a catalyst placed inside thereof, under stirring as required.

Hereinafter, each component that is used in the present invention is described.

<Primary Alcohol>

In the present invention, in terms of the usefulness, as a fragrance material, of the aldehyde to be produced, the primary alcohol to be used as a raw material has at least 4 carbon atoms, preferably at least 6 carbon atoms, and more preferably at least 8 carbon atoms. Furthermore, in terms of the usefulness, as a fragrance material, of the aldehyde to be produced, the primary alcohol has not more than 18 carbon atoms, preferably not more than 15 carbon atoms, and more preferably not more than 12 carbon atoms. Moreover, in terms of the usefulness, as a fragrance material, of the aldehyde to be produced, the primary alcohol has preferably 6 to 15 carbon atoms, more preferably 8 to 15 carbon atoms, and further preferably 8 to 12 carbon atoms.

The primary alcohol can be either a saturated aliphatic alcohol or an unsaturated aliphatic alcohol. However, in terms of the usefulness, as a fragrance material, of the aldehyde to be produced, a saturated aliphatic alcohol is preferred.

The saturated aliphatic alcohol has a hydroxy group in a linear, branched, or cyclic alkane and is preferably one having a hydroxy group in a linear alkane in terms of the usefulness, as a fragrance material, of the aldehyde to be produced.

Examples of the saturated aliphatic alcohol include butanol, hexyl alcohol, isohexyl alcohol, octyl alcohol, isooctyl alcohol, 2-ethylhexyl alcohol, nonyl alcohol, isononyl alcohol, 3,5,5-trimethylhexyl alcohol, decyl alcohol, undecyl alcohol, 3,7-dimethyloctyl alcohol, 2-propyl heptyl alcohol, lauryl alcohol, myristyl alcohol, geraniol, cyclopentyl methanol, cyclopentenyl methanol, cyclohexyl methanol, and cyclohexenyl methanol. Among them, in terms of the usefulness, as a fragrance, of the aldehyde to be produced, the saturated aliphatic alcohol is preferably hexyl alcohol, isohexyl alcohol, octyl alcohol, isooctyl alcohol, 2-ethylhexyl alcohol, nonyl alcohol, isononyl alcohol, 3,5,5-trimethylhexyl alcohol, decyl alcohol, undecyl alcohol, 3,7-dimethyloctyl alcohol, 2-propyl heptyl alcohol, lauryl alcohol, myristyl alcohol, or geraniol, more preferably octyl alcohol, nonyl alcohol, decyl alcohol, undecyl alcohol, or lauryl alcohol.

The unsaturated aliphatic alcohol has a hydroxy group in a linear, branched, or cyclic alkene or alkyne. In terms of the usefulness, as a fragrance material, of the aldehyde to be produced, the unsaturated aliphatic alcohol is preferably one having a hydroxy group in a linear, branched, or cyclic alkene, more preferably one having a hydroxy group in a linear alkene.

<Inert Gas>

The raw material gas of the present invention may further contain an inert gas as described above. In terms of the affinity and reactivity with a catalyst, the inert gas is preferably nitrogen or rare gas (Group 18 element), more preferably nitrogen. Examples of the rare gas include argon and helium and it is preferably argon.

<Dehydrogenation Catalyst>

The dehydrogenation catalyst that is used in the present invention is a catalyst containing copper and iron as active species in terms of improving the alcohol conversion rate, the activity of the catalyst, and the durability of the catalyst obtained at the partial pressure of the water described above.

Although the cause is not clear, it is thought that when copper forms a compound oxide together with iron, the compound oxide undergoes some sort of interaction with water, which suppresses the production of a compound to be a precursor of a high molecular weight component that reduces the activity of the catalyst.

Furthermore, in terms of the activity and durability of the catalyst, it is preferable that the dehydrogenation catalyst that is used in the present invention further contain a metal element in addition to copper and iron. Specifically, the dehydrogenation catalyst is composed of preferably three components or at least four components containing a metal element in addition to copper and iron. The metal element to be contained in addition to copper and iron is preferably at least one selected from the group consisting of zinc, chromium, cobalt, nickel, manganese, aluminum, silicic acid, and titanium. The metal element in addition to copper and iron is preferably aluminum and zinc, further preferably aluminum in terms of the aldehyde selectivity. The dehydrogenation catalyst is preferably a copper-iron-aluminum catalyst, a copper-iron-aluminum-zinc catalyst, etc., more preferably a copper-iron-aluminum catalyst.

Moreover, the dehydrogenation catalyst is preferably an oxide in terms of the activity and durability of the catalyst.

With respect to the dehydrogenation catalyst, an active material of the dehydrogenation catalyst may be supported on a carrier or the active material may be mixed with a carrier. Examples of the carrier include oxides and hydroxides of aluminum, zinc, silicon, titanium, etc. as well as alumina, silica gel, titania, silica-alumina, zeolite, diatomaceous earth, magnesia, calcia, zirconia, etc. Preferred carriers are an oxide and hydroxide of aluminum, zinc, silicon, or titanium, zeolite, and silica-alumina. In terms of the alcohol conversion rate, the carrier is more preferably an oxide or hydroxide of zinc or aluminum, further preferably an oxide of zinc or an oxide or hydroxide of aluminum.

In terms of the activity, selectivity, and durability of the dehydrogenation catalyst, the catalyst is preferably a catalyst containing copper, iron, and aluminum as a composition also including a carrier, and the atomic ratio (copper/iron/aluminum) of the elements that compose the catalyst is preferably 1/0.4 to 2.5/0.5 to 5.0, more preferably 1/0.5 to 1.0/1.5 to 3.5, and further preferably 1/0.5 to 1.0/2.5 to 3.0. Furthermore, when the dehydrogenation catalyst contains copper, iron, and aluminum as a composition also including a carrier, the atomic ratio of iron to copper (Fe/Cu) is, in terms of the activity and selectivity of the catalyst, preferably at least 0.4, more preferably at least 0.5, and in terms of the durability of the catalyst, preferably not more than 3.5, more preferably not more than 2.5. Moreover, the atomic ratio of iron to copper (Fe/Cu) is preferably 0.4 to 3.5, more preferably 0.5 to 2.5.

Furthermore, when the dehydrogenation catalyst contains copper, iron, and aluminum as a composition also including a carrier, the atomic ratio of aluminum to copper (Al/Cu) is preferably at least 0.5, more preferably at least 1.5 in terms of the activity and selectivity of the catalyst. Moreover, Al/Cu is preferably not more than 5.0, more preferably not more than 3.5 in terms of the durability of the catalyst. Furthermore, the atomic ratio of aluminum to copper (Al/Cu) is preferably 0.5 to 5.0, more preferably 1.5 to 3.5.

In terms of the activity, selectivity, and durability of the catalyst, the dehydrogenation catalyst also is preferably a catalyst containing copper, iron, aluminum, and zinc as a composition also including a carrier, and the atomic ratio (copper/iron/aluminum/zinc) of the elements that compose the catalyst is preferably 1/0.4 to 3.5/0.5 to 5.0/0.01 to 0.20, more preferably 1/0.5 to 2.5/1.0 to 3.0/0.02 to 0.10. Furthermore, when the dehydrogenation catalyst contains copper, iron, aluminum, and zinc as a composition also including a carrier, the atomic ratio of iron to copper (Fe/Cu) is, in terms of the activity and selectivity of the catalyst, preferably at least 0.4, more preferably at least 0.5, and in terms of the durability of the catalyst, preferably not more than 3.5, more preferably not more than 2.5. Moreover, the atom ratio of iron to copper (Fe/Cu) is preferably 0.4 to 3.5, more preferably 0.5 to 2.5.

When the dehydrogenation catalyst contains copper, iron, aluminum, and zinc as a composition also including a carrier, the atomic ratio of aluminum to copper (Al/Cu) is preferably at least 0.5, more preferably at least 1.0, and further preferably at least 1.5 in terms of the activity and selectivity of the catalyst. Furthermore, Al/Cu is preferably not more than 5.0, more preferably not more than 3.0, and further preferably not more than 2.0 in terms of the durability of the catalyst. Moreover, the atomic ratio of aluminum to copper (Al/Cu) is preferably 0.5 to 5.0, more preferably 1.0 to 3.0, and further preferably 1.5 to 2.0.

When the dehydrogenation catalyst contains copper, iron, aluminum, and zinc as a composition also including a carrier, the atomic ratio of zinc to copper (Zn/Cu) is preferably at least 0.01, more preferably at least 0.02, and further preferably at least 0.03 in terms of the activity and selectivity of the catalyst. Furthermore, Zn/Cu is preferably not more than 0.20, more preferably not more than 0.10, and further preferably not more than 0.07 in terms of the durability of the catalyst. Moreover, the atomic ratio of zinc to copper (Zn/Cu) is preferably 0.01 to 0.20, more preferably 0.02 to 0.10, and further preferably 0.03 to 0.07.

<Method for Preparing Dehydrogenation Catalyst>

A dehydrogenation catalyst can be prepared by a known method such as a coprecipitation method, a kneading method, or an alkoxide method.

When a dehydrogenation catalyst is prepared by the coprecipitation method, a liquid mixture of a metal salt that contains metal components of the components of a target dehydrogenation catalyst at an atomic ratio to be obtained in the dehydrogenation catalyst is prepared, a precipitant is added thereto, and then the liquid mixture is set to have preferably a pH (25° C.) of 8 to 12, thus obtaining a precipitate. Further, the precipitate thus obtained is filtered to be separated, which is washed with water and then is dried preferably at 90 to 150° C. The dried product thus obtained is calcined preferably at 500 to 1500° C., more preferably 600 to 1000° C. Thus the dehydrogenation catalyst is prepared.

The metal salt used herein is generally sulfate, nitrate, ammonium complex salt, acetate, or chloride. Furthermore, an alkaline aqueous solution of, for example, ammonia, urea, ammonium carbonate, sodium bicarbonate, sodium carbonate, or sodium hydroxide is used as a precipitant.

The method of producing the powdered catalyst is not limited as long as dehydration is facilitated. However, it is preferable that a catalyst containing copper-iron-aluminum, which is a preferred aspect of the catalyst, be produced by the method in which the following first to third steps are carried out in this order.

<First Step>

In the first step, at least one (hereinafter referred to as a "carrier") selected from the group consisting of oxides and hydroxides of aluminum, silicon, titanium, zirconium, magnesium, and iron, zeolite, and silica-alumina is suspended in an aqueous medium, a water-soluble copper salt and a water-soluble iron salt are reacted with an alkaline substance in the suspension, and thereby a copper compound and an iron compound are precipitated on the surface of the carrier.

First, the water-soluble copper salt and the water-soluble iron salt are dissolved in water in such a manner as to have an atomic ratio (Cu/Fe) of 1/0.4 to 2.5, and then the carrier is suspended in this aqueous solution in such a manner that the atomic ratio of Cu/metallic atom of the carrier is 1/0.1 to 3.0. This suspension is heated to 60 to 120° C., an aqueous solution of an alkaline substance whose amount corresponds to the total equivalent number of copper and iron ions is added thereto, and the copper compound and the iron compound are precipitated on the surface of the catalyst carrier.

Examples of the water-soluble copper salt that is used in the present invention include cupric sulfate, cupric chloride, cupric nitrate, etc. and a mixture thereof may be used. Examples of the water-soluble iron salt that is used in the present invention include ferrous sulfate, ferrous chloride, ferrous nitrate, etc. and a mixture thereof may be used but it is preferable to use ferrous sulfate from the economic viewpoint.

Examples of the alkaline substance that is used in the present invention include a hydroxide or carbonate of alkali metal or alkaline earth metal. The method of adding the alkaline substance to the suspension is not particularly limited. Generally, however, in consideration of operability, such an alkaline substance is added in the form of an aqueous solution. In the case of using a hydroxide of alkali metal or alkaline earth metal as the alkaline substance, it is desirable to drop it slowly in order also to prevent the filterability of the precipitated catalyst from being impaired. In the present invention, it is preferable to use a carbonate of alkali metal. The concentration of such an alkaline substance can be selected arbitrarily. However, when the productivity of the catalyst is taken into consideration, a higher concentration of precipitant also can be used. For example, in the case of sodium carbonate, an aqueous solution with a concentration of 20 to 25% by mass is suitable.

At least one selected from the group consisting of oxides and hydroxides of aluminum, silicon, titanium, zirconium, magnesium, and iron, zeolite, and silica-alumina, which is used as a carrier in the first step, may be used without being further processed after being prepared in a reaction vessel, or one that has been separately prepared beforehand may be used. Preferably, such a carrier to be used herein is one that has relatively uniform particle diameter. An average particle diameter of the carrier is 0.1 μm to 500 μm, preferably 0.4 μm to 50 μm. As a method of preparing the carrier inside a reaction vessel, there is a method in which after ferric salt, for example, sulfate, nitrate, hydrochloride, etc., is dissolved in water in an amount to be used as the carrier, a carbonate of alkali metal, for example, a sodium carbonate aqueous solution, is dropped in an amount corresponding to the equivalent number of iron ions at a temperature of at least 60° C. and thereby neutralization is achieved. In the case of this method, without refining the precipitation produced therein, a copper salt and an iron salt are fed into the slurry thereof and thereby the first step can be carried out continuously. In the case of using a carrier with uniform physical properties, a catalyst with more stable performance can be produced. Thus, it is more advantageous to use carriers with uniform physical properties for production on an industrial scale.

<Second Step>

In the second step, water-soluble aluminum and an alkaline substance are reacted with each other in the suspension obtained in the first step and thereby an aluminum compound is precipitated on the surfaces of the solid particles that exist in the suspension obtained in the first step.

The second step is carried out by dropping, into the suspension obtained in the first step, (a) an aqueous solution of water-soluble aluminum salt (where the Al amount in this case with respect to the water-soluble copper salt used in the first step is 1/0.1 to 5.0, preferably 1/0.5 to 3.0 in the atomic ratio) and (b) an alkaline substance in an amount corresponding to the equivalent number of the aluminum ions described in (a), and precipitating an aluminum compound while maintaining the temperature of the suspension at 60 to 120° C.

Examples of the water-soluble aluminum salt described in (a) above include aluminum sulfate, aluminum chloride, aluminum nitrate, and various alums. Among them, aluminum sulfate is preferred. Furthermore, a mixture thereof may be used.

Examples of the alkaline substance described in (b) above include the alkaline substances that are used in the same manner in the first step. With respect to the method of adding the alkaline substance, it is preferable to add it in the form of an aqueous solution in terms of operability. The concentration thereof is not particularly limited but it is preferable that the aqueous solution have a concentration of 20 to 25% by mass from the economic viewpoint. With respect to the method of adding the alkaline substance, it is preferable that in order to prevent a rapid change in pH of the suspension, the aqueous solution described in (a) above and the alkaline substance described in (b) above or the aqueous solution thereof be simultaneously added to the suspension obtained in the first step.

An embodiment of the second step is, for example, as follows. (a) Only an aluminum compound is precipitated. (b) An aluminum compound and a copper compound are precipitated simultaneously. (c) In the first step, an aluminum compound and a copper compound are precipitated simultaneously and then in the second step, an aluminum compound is precipitated. (d) A combination of these steps is carried out repeatedly for a plurality of times. With respect to the suspension obtained by the method described above, the pH thereof is adjusted to be at least 7.0, and then it is aged for 0 to 8 hours.

<Third Step>

In the third step, the precipitate obtained in the second step is separated by a ordinary method and then is washed with water. The slurry or powdered thus obtained is dried and calcined. The calcining temperature is usually in the range between 100° C. and 1200° C., preferably between 400° C. and 900° C. The calcining time is not particularly limited but economically it is preferably not more than 10 hours. The product obtained after calcining may be pulverized but it can also be used as a catalyst immediately after calcining without being pulverized.

<Form of Dehydrogenation Catalyst>

Examples of the dehydrogenation catalyst include catalysts in a powdered state, pellet-type catalysts made of active materials formed into pellet-shaped molded products by, for example, tablet molding, noodle-type catalysts formed into noodle-shaped molded products by, for example, extrusion molding, and film-type catalysts with an active material fixed on a substrate with a binder. In the present invention, in terms of the productivity of an aldehyde, the dehydrogenation catalyst is preferably a pellet-type catalyst, a noodle-type catalyst, or a film-type catalyst, more preferably a pellet-type catalyst or a film-type catalyst. The above-mentioned active material is kneaded together with a binder such as carboxymethylcellulose sodium salt and the mixture thus obtained is dried, which thereafter may be molded. In the case of the pellet type, it has a columnar shape and it may have a diameter of, for example, 0.5 mm to 50 mm and a height of 0.5 mm to 50 mm.

In the case of the film-type catalyst, it is not limited as long as it is a dehydrogenation catalyst in a film-like form. However, it is, for example, a dehydrogenation catalyst having a catalyst layer with a thickness of not more than 1 mm on a support. In this case, in terms of suppressing the retention inside pores of the catalyst layer to obtain a high aldehyde selectivity, the thickness of the dehydrogenation catalyst layer having a film-like form is preferably not more than 400 μm, more preferably not more than 100 μm, further preferably not more than 50 μm, and still further preferably not more than 30 μm. Moreover, in terms of securing the strength of the film-like form and thereby obtaining the durability in terms of strength, the thickness of the dehydrogenation catalyst layer having a film-like form is preferably at least 0.01 μm, more preferably at least 1 μm.

In the case of the film-type catalyst, in terms of obtaining a high aldehyde selectivity, the mass per unit area of the catalyst layer including the binder is, for example, at least $0.015$ $g/m^2$, preferably at least $1.5$ $g/m^2$, more preferably at least $10$ $g/m^2$, and further preferably at least $15$ $g/m^2$. Furthermore, in the case of the film-type catalyst, in terms of obtaining a high aldehyde selectivity, the mass per unit area of the catalyst layer including the binder is, for example, not more than $600$ $g/m^2$, preferably not more than $75$ $g/m^2$, more preferably not more than $50$ $g/m^2$, and further preferably not more than $30$ $g/m^2$. Moreover, in the case of the film-type catalyst, in terms of obtaining a high aldehyde selectivity, the mass per unit area of the catalyst layer including the binder is, for example, $0.015$ $g/m^2$ to $600$ $g/m^2$, preferably $1.5$ $g/m^2$ to $75$ $g/m^2$, more preferably $10$ $g/m^2$ to $50$ $g/m^2$, and further preferably $15$ $g/m^2$ to $30$ $g/m^2$.

In the case of the film-type catalyst, in terms of obtaining a high aldehyde selectivity, the mass per unit area of a copper-based catalyst in the catalyst layer is, for example, at least $0.01$ $g/m^2$, preferably at least $1.1$ $g/m^2$, more preferably at least $5$ $g/m^2$, and further preferably at least $10$ $g/m^2$. Furthermore, in the case of the film-type catalyst, in terms of obtaining a high aldehyde selectivity, the mass per unit area of the copper-based catalyst in the catalyst layer is, for example, not more than $440$ $g/m^2$, preferably not more than $55$ $g/m^2$, more preferably not more than $30$ $g/m^2$, and further preferably not more than $20$ $g/m^2$. Moreover, in the case of the film-type catalyst, in terms of obtaining a high aldehyde selectivity, the mass per unit area of the copper-based catalyst in the catalyst layer is, for example, $0.01$ $g/m^2$ to $440$ $g/m^2$, preferably $1.1$ $g/m^2$ to $55$ $g/m^2$, more preferably $5$ $g/m^2$ to $30$ $g/m^2$, and further preferably $10$ $g/m^2$ to $20$ $g/m^2$.

For the structure of the film-type dehydrogenation catalyst, a structure with a form corresponding to the reactor shape can be selected. Examples of the film-type dehydrogenation catalyst include a dehydrogenation catalyst coating layer formed on a tube inner wall surface and a dehydrogenation catalyst molded in the form of a thin plate that divides the inside of a tube into a plurality of flow passages running in the axial direction. Each of them can be used suitably for a tubular flow reactor. Furthermore, the film-type dehydrogenation catalyst may be, for example, a dehydrogenation catalyst coating layer formed on the surface of an open fin-shaped flat plate placed inside a vessel. Such a film-type dehydrogenation catalyst can be used suitably in the case of a vessel-type reactor. In terms of providing a catalyst body surface, on which a reaction material is supplied and products are collected, as large as possible, and allowing the reaction to proceed efficiently, the film-type dehydrogenation catalyst is preferably provided on bundled tubes each having an inner diameter of several millimeters to several dozen millimeters, or on an inner wall surface of a honeycomb structural body having a cell density of several dozen cells to several hundred cells per square inch.

In order to form film-type dehydrogenation catalysts with such structures as described above, in terms of obtaining both a thin catalyst layer and a high mechanical strength at the same time, it is preferable to fix a catalytic active material to the surface of a support.

For the support, a material having rigidity such as metal is preferred. Specific examples thereof include a metallic foil, a carbon composite, and clay. Among them, a metallic foil is preferred. The metallic foil is preferably, for example, a copper foil, a stainless steel foil, or an aluminum foil, more preferably a copper foil or a stainless steel foil.

Examples of the film-type dehydrogenation catalyst include a catalyst with a catalytic active material fixed onto a support by applying a mixture of the catalytic active material and a binder onto the support and then curing the binder.

Examples of the binder used herein include high molecular or inorganic compounds, specifically, cellulose-based resins such as carboxymethyl cellulose and hydroxyethyl cellulose, fluorine-based resins such as polytetrafluoroethylene and polyvinylidene fluoride, urethane resin, epoxy resin, polyester resin, phenolic resin, melamine resin, silicone resin, high molecular compounds such as polycarbotitanium and polytitanocarbosilane, and inorganic compound sols such as silica and alumina.

In terms of the durability of the catalyst, the binder is preferably phenolic resin, polycarbotitanium, or polytitanocarbosilane, more preferably phenolic resin or polytitanocarbosilane, and further preferably polytitanocarbosilane.

Examples of the method for obtaining a film-type dehydrogenation catalyst include a method for obtaining a film-type dehydrogenation catalyst by forming a coating layer containing a catalytic active material on the surface of a support having, for example, a tubular-, sheet-, or honeycomb-shape. In this case, for the coating method, a conventionally known method can be used and examples thereof include a physical vapor deposition method such as sputtering, a chemical vapor deposition method, an impregnation method using a solution system, as well as a method of applying a mixture of a catalytic active material and a binder using a bar coater, a blade, spraying, dipping, spinning, gravure, die coating, etc.

<Aldehyde Production Apparatus>

A reaction apparatus that can be used in method for producing an aldehyde according to this embodiment is described. The reaction apparatus that can be used in the method for producing the aldehyde according to this embodiment is not limited to that described below.

<First Apparatus Configuration>

FIG. 1 shows a reaction apparatus 10 that is an example of the first apparatus configuration. This reaction apparatus 10 is equipped with a reaction unit 14 that is provided with a catalyst (not shown in the FIGURE) inside thereof, and a raw material alcohol feed pipe 31 extending from a raw material alcohol feeder 11 is connected to the upstream end of the reaction unit 14. The raw material alcohol feed pipe 31 is provided with a raw material feed pump 12 and a raw material preheating unit 13 in this order from the upstream side.

A gas feed pipe 32 extending from a gas feeder 21 and a water feed pipe 33 extending from a water feeder 24 each are connected to a site located on the downstream side of the raw material preheating unit 13 in the raw material alcohol feed pipe 31. The gas feed pipe 32 is provided with a gas flow rate adjuster 22 and a gas preheating unit 23 in this order from the upstream side. The water feed pipe 33 is provided with a water feed pump 25 and a water preheating unit 26 in this order from a distillation side.

A product collection pipe 34 extends from the downstream end of the reaction unit 14 and is connected to a gas-liquid separation unit 17. The product collection pipe 34 is provided with a cooling unit 16.

A liquid product collection pipe 35 and an exhaust gas discharge pipe 36 each extend from the gas-liquid separation unit 17.

The reaction apparatus 10 is provided with a heating unit 15 capable of temperature control as a heat source for the reaction unit 14, the raw material preheating unit 13, the gas preheating unit 23, and the water preheating unit 26.

In this reaction apparatus 10, a primary alcohol as a raw material is fed to the raw material preheating unit 13 continuously from the raw material alcohol feeder 11 by the raw material feed pump 12. In this case, the alcohol as a raw material is heated into a gaseous state in the raw material preheating unit 13, with the heating unit 15 being used as the heat source.

Water is fed to the water preheating unit 26 continuously from the water feeder 24 by the water feed pump 25. In this case, the water is heated into a vaporized state in the water preheating unit 26, with the heating unit 15 being used as the heat source.

An inert gas is fed to the gas preheating unit 23 continuously from the gas feeder 21. In this case, the inert gas is heated in the gas preheating unit 23, with the heating unit 15 being used as the heat source.

The gaseous primary alcohol fed from the raw material preheating unit 13, the gaseous water fed from the water preheating unit 26, and the inert gas fed from the gas preheating unit 23 join together at the site where the raw material alcohol feed pipe 31, the water feed pipe 33, and the gas feed pipe 32 are connected together and compose a reaction raw material gas. A reaction fluid is fed to the reaction unit 14.

The reaction fluid fed to the reaction unit 14 is heated inside the reaction unit 14, with the heating unit 15 being used as the heat source, and then comes into contact with a dehydrogenation catalyst. Thus the primary alcohol contained in the reaction fluid is dehydrogenated. As a result, the reaction fluid obtained after dehydrogenation contains an aldehyde produced by dehydrogenation of the primary alcohol, hydrogen, unreacted primary alcohol, water, and the inert gas.

The reaction fluid coming out from the reaction unit 14 is fed to the gas-liquid separation unit 17 through the cooling unit 16. The reaction fluid is condensed in the cooling unit 16 and is divided, in the gas-liquid separation unit 17, into a liquid component containing the aldehyde, unreacted primary alcohol, and water and a gas component composed of the hydrogen and inert gas. The former is collected through the liquid product collection pipe 35, while the latter is discharged through the exhaust gas discharge pipe 36.

With respect to the embodiment described above, the present invention further discloses the following method for producing an aldehyde.

<1> An method for producing an aldehyde comprising bringing a raw material gas containing a primary alcohol having 4 to 18 carbon atoms and water into contact with a dehydrogenation catalyst containing copper and iron so as to dehydrogenate the alcohol contained in the raw material gas, thereby obtaining an aldehyde, wherein the raw material gas has a water partial pressure of 0.2 kPa to 99 kPa.

<2> The method for producing the aldehyde according to the item <1>, wherein the water partial pressure of the raw material gas is preferably at least 1 kPa, more preferably at least 10 kPa, and further preferably at least 40 kPa, preferably not more than 90 kPa, more preferably not more than 80 kPa, and further preferably not more than 60 kPa, as well as preferably 1 kPa to 90 kPa, more preferably 10 kPa to 80 kPa, further preferably 40 kPa to 80 kPa, and still further preferably 40 kPa to 60 kPa.

<3> The method for producing the aldehyde according to the item <1>, wherein the water concentration in the reaction raw material gas is preferably at least 0.05 mol/m$^3$, more preferably at least 0.11 mol/m$^3$, and further preferably at least 0.40 mol/m$^3$, as well as preferably not more than 23 mol/m$^3$, more preferably not more than 20 mol/m$^3$, further preferably not more than 18 mol/m$^3$, and still further preferably not more than 14 mol/m$^3$.

<4> The method for producing the aldehyde according to any one of the items <1> to <3>, wherein the primary alcohol has preferably at least 6 carbon atoms, more preferably at least 8 carbon atoms, preferably not more than 15 carbon atoms, more preferably not more than 12 carbon atoms, as well as preferably 6 to 15 carbon atoms, more preferably 8 to 15 carbon atoms, and further preferably 8 to 12 carbon atoms.

<5> The method for producing the aldehyde according to any one of the items <1> to <4>, wherein the primary alcohol is preferably a saturated aliphatic alcohol, more preferably an alcohol having a hydroxy group in a linear alkane.

<6> The method for producing the aldehyde according to any one of the items <1> to <5>, wherein the reaction temperature is preferably at least 200° C., more preferably at least 220° C., and further preferably at least 240° C., preferably not more than 300° C., more preferably not more than 270° C., as well as preferably 200° C. to 300° C., more preferably 220° C. to 270° C., and further preferably 240° C. to 270° C.

<7> The method for producing the aldehyde according to any one of the items <1> to <6>, wherein the pressure for dehydrogenation under which the raw material gas is brought into contact with the dehydrogenation catalyst is preferably not more than 102 kPa, more preferably 10 kPa to 102 kPa in absolute pressure.

<8> The method for producing the aldehyde according to any one of the items <1> to <7>, wherein in the case where the primary alcohol of the raw material has not more than 10 carbon atoms, the pressure for dehydrogenation is preferably at least 80 kPa, more preferably at least 90 kPa, preferably not more than 102 kPa, as well as preferably 80 kPa to 102 kPa, more preferably 90 kPa to 102 kPa in absolute pressure.

<9> The method for producing the aldehyde according to any one of the items <1> to <7>, wherein in the case where the primary alcohol of the raw material has at least 11 carbon atoms, the pressure for dehydrogenation is preferably at least 10 kPa, more preferably at least 13 kPa, preferably not more than 102 kPa, as well as preferably 10 kPa to 102 kPa, more preferably 13 kPa to 102 kPa in absolute pressure.

<10> The method for producing the aldehyde according to any one of the items <1> to <9>, wherein the dehydrogenation catalyst contains at least 2 metal elements including copper and another metal element, preferably further contains a metal element in addition to copper and iron, and preferably contains three components containing a metal element in addition to copper and iron or at least four components containing metal elements in addition to copper and iron, and the dehydrogenation catalyst is more preferably a copper-iron-aluminum catalyst or a copper-iron-aluminum-zinc catalyst, further preferably a copper-iron-aluminum catalyst.

<11> The method for producing the aldehyde according to the item <10>, wherein the metal element contained in addition to copper and iron is preferably at least one selected from the group consisting of zinc, chromium, cobalt, nickel, manganese, aluminum, silicic acid, and titanium, more preferably aluminum and zinc, and further preferably aluminum.

<12> The method for producing the aldehyde according to any one of the items <1> to <11>, wherein the dehydrogenation catalyst is supported by a carrier.

<13> The method for producing the aldehyde according to the item <12>, wherein the carrier is alumina, silica gel, titania, silica-alumina, zeolite, diatomaceous earth, magnesia, calcia, or zirconia, preferably an oxide or hydroxide of zinc or aluminum, and more preferably an oxide of zinc or an oxide or hydroxide of aluminum.

<14> The method for producing the aldehyde according to any one of the items <1> to <13>, wherein the dehydrogenation catalyst is a pellet-type catalyst or a film-type catalyst.

<15> The method for producing the aldehyde according to any one of the items <1> to <14>, wherein the partial pressure of the primary alcohol of the raw material gas is preferably not more than 50 kPa, more preferably not more than 30 kPa, and further preferably not more than 20 kPa, preferably at least 1 kPa, more preferably at least 5 kPa, as well as preferably kPa to 50 kPa, more preferably 5 kPa to 30 kPa, and further preferably 5 kPa to 20 kPa.

<16> The method for producing the aldehyde according to any one of the items <1> to <15>, wherein the raw material gas further contains an inert gas, preferably nitrogen or a rare gas (Group 18 Element, (for example, argon or helium, preferably argon)), and more preferably nitrogen.

<17> The method for producing the aldehyde according to any one of the items <1> to <16>, wherein a reactor that is used in a dehydrogenation step is a tubular flow reactor.

<18> The method for producing the aldehyde according to any one of the items <1> to <17>, wherein the primary alcohol contained in the raw material gas is vaporized beforehand, preferably vaporized beforehand by a means such as heating or decompression, and more preferably vaporized beforehand by heating (heating to preferably at least 200° C., more preferably at least 220° C., and further preferably at least 230° C., as well as preferably not more than 500° C., more preferably not more than 400° C., and further preferably not more than 300° C.).

<19> The method for producing the aldehyde according to any one of the items <1> to <18>, wherein the water contained in the raw material gas is vaporized beforehand, preferably vaporized beforehand by a means such as heating or decompression, and more preferably vaporized beforehand by heating.

<20> The method for producing the aldehyde according to any one of the items <1> to <19>, wherein the raw material gas containing the primary alcohol and water is prepared by a method in which the primary alcohol and water are mixed together after each of them is vaporized independently or a method in which they are mixed together before being vaporized.

<21> The method for producing the aldehyde according to the item <13> or <14>, wherein in terms of (copper/iron/aluminum), the dehydrogenation catalyst as a composition also including a carrier has an atomic ratio of copper/iron/aluminum of preferably 1/0.4 to 2.5/0.5 to 5.0, more preferably 1/0.5 to 1.0/1.5 to 3.5, and further preferably 1/0.5 to 1.0/2.5 to 3.0).

<22> The method for producing the aldehyde according to any one of the items <1> to <21>, wherein the step for bringing the gas into contact with the dehydrogenation catalyst is carried out by continuously passing the gas through the reactor charged with the dehydrogenation catalyst.

EXAMPLES

Hereinafter, the present invention is described in further detail with reference to examples, but the present invention is not limited by these examples.

With respect to each of the aldehyde production tests in the examples and comparative examples described below, the alcohol conversion rate and the catalyst durability were determined. The conversion rate of a primary alcohol and the selectivity as well as the catalyst durability each were determined as follows.

<Alcohol Conversion Rate and Selectivity>

A reaction fluid collected from the reaction unit 14 was condensed and thereby a liquid product was collected. With respect to the liquid product thus collected, the concentrations of the primary alcohol and aldehyde were determined by a gas chromatography analysis. In the case where the liquid product that had been collected underwent phase separation, the concentration of the primary alcohol was determined with respect to the top phase (oil phase) by the gas chromatography analysis. Then, with the amount of the alcohol fed as a raw material being considered as 100%, the value calculated by a formula (100−Primary Alcohol Concentration) (%) was taken as the conversion rate.

Furthermore, the value calculated by a formula 100×(Aldehyde Concentration/Conversion Rate) (%) was taken as the selectivity.

Alcohol Conversion Rate [%]=100−(Primary Alcohol Concentration %)

Selectivity [%]=100×(Aldehyde Concentration/Conversion Rate)

<Catalyst Durability>

The reaction fluid collected from the reaction unit 14 was condensed and the alcohol conversion rate was calculated by the above-mentioned method. After the reaction temperature, the reaction pressure, and each feed flow rate had reached preset values, the amount of change in conversion rate per unit time from 6 hours to 24 hours was calculated by the least-squares method, which was taken as the catalyst durability. With respect to the durability, a smaller absolute value thereof allows a higher conversion rate to be maintained over an extended period of time and therefore is preferable.

A gas chromatograph "6890" (manufactured by Agilent Technologies) equipped with a capillary column "DB-1" (30 m×0.25 mm×0.25 μm, manufactured by Agilent Technologies) was used for the gas chromatography analysis carried out with respect to the conversion rate of the primary alcohol and the catalyst durability. With respect to the conditions for temperature increase, the temperature was increased at 10° C./min from 100 to 200° C. and at 2° C./min from 200 to 280° C. and was maintained at 280° C. for 10 minutes. The carrier gas used herein was helium.

Production Example 1

Production of Copper-Iron-Aluminum Pellet-Type Catalyst

<Powdered Catalyst Production Step>

Water (300 g), $CuSO_4.5H_2O$ (48 g), $FeSO_4.7H_2O$ (59 g), and aluminum hydroxide "HIGILITE H-42M" (manufactured by Showa Denko, 12.14 g) were placed in a reactor equipped with a reflux condenser, and the temperature was increased to 95° C. while stirring. The temperature was maintained at 95 to 97° C. for one hour (Fe/Cu (atomic ratio)= 0.75/1 and Cu/aluminum of aluminum hydroxide (atomic ratio)=1/0.7). Subsequently, while this temperature was maintained, a solution containing $Na_2CO_3$ (44.8 g, 1 equivalent with respect to the total equivalent number of copper and iron ions) dissolved in water (150 g) was dropped for 80 minutes. Blue-green precipitation that was visible in the mixture was gradually changed in color to brown and ultimately became black.

While the temperature of the mixture was maintained at 95 to 97° C., dropping of a solution 1 and a solution 2 into the mixture was started simultaneously. The solution 1 (Fe/Cu (atomic ratio)=0.75/1 and Cu/aluminum of aluminum hydroxide (atomic ratio)=1/0.7) contained $CuSO_4.5H_2O$ (4.8 g) and $Al_2(SO_4)_2.16H_2O$ (46.8 g) dissolved in water (109.2 g) and the solution 2 (22% by mass, 1 equivalent with respect to the total equivalent number of copper and iron ions) contained $Na_2CO_3$ (27.6 g) dissolved in water (98.2 g). Dropping of the solution 1 was completed in 60 minutes while dropping of the solution 2 was completed in 30 minutes. A solution containing $Al_2(SO_4)_2.16H_2O$ (23.4 g) dissolved in water (53.5 g) was dropped into the mixture over 30 minutes (Cu/aluminum of aluminum hydroxide (atomic ratio)=1/2.1). Furthermore, 10% by mass of NaOH aqueous solution was dropped into the mixture and the pH of the mixture was adjusted to 10.5. The mixture was aged for one hour. After the completion of aging, the mixture was subjected to filtration under reduced pressure and thereby a precipitate was obtained. After the precipitate thus obtained was washed three times with 450 mL of water, it was calcined in the air at 750° C. for one hour, and thereby a copper-based powdered catalyst (a copper-iron-aluminum catalyst, the carrier: aluminum oxide, the particle diameter of the carrier: 1 μm, Fe/Cu (atomic ratio)=0.75/1, Al/Cu (atomic ratio)=2.8/1) was obtained.

Production Example 2

Production of Copper-Iron-Aluminum Pellet-Type Catalyst

A carboxymethylcellulose sodium salt was added to the copper-based powdered catalyst obtained in Production Example 1 above, and the mixture thus obtained was kneaded while deionized water was added thereto. After the mixture thus obtained was dried at 110° C., it was tablet-molded into a columnar shape. The molded product thus obtained was calcined in the air at 400° C. for two hours and thereby a pellet-type catalyst (4.8 mm in diameter and 4.7 mm in height) was obtained.

Production Example 3

Production of Copper-Iron-Aluminum Film-Type Catalyst 75 parts by mass of the copper-based powdered catalyst obtained in the powdered catalyst production step in Production Example 1, 25 parts by mass of polytitanocarbosilane "Tyranno Coat VN-100" (manufactured by Ube Industries, Ltd.) as a binder, and 60 parts by mass of methyl ethyl ketone were mixed together in a ball mill and thereby a coating material was obtained. The coating material was applied onto one side of a copper foil (40 μm in thickness and 15 cm×33 cm in width) (a support) with a bar coater. The catalyst layer coating material thus obtained on the copper foil was dried at 130° C. for one minute and then was heated in a nitrogen atmosphere at 250° C. for 90 minutes. Thus the binder contained in the coating material was cured. The catalyst layer coating material was applied onto the other side of the copper foil as in the above, and it was dried and heated as in the above. As a result, a film-type dehydrogenation catalyst with a 15-μm thick catalyst layer fixed to each side of the copper foil was obtained. The catalyst layer had a mass per unit area of 23.7 g/m² including the binder and the copper-based catalyst in the catalyst layer had a mass per unit area of 17.8 g/m².

Production Example 4

Production of Copper-Iron-Aluminum-Zinc Film-Type Catalyst 75 parts by mass of a copper-based catalyst "N2A3" (manufactured by JGC Catalysts and Chemicals Ltd., the composition ratio: $CuO:Fe_2O_3:Al_2O_3:ZnO=30.3:30.3:35.9:1.5$. Copper-iron-aluminum-zinc catalyst, the average particle diameter: 10 μm, Fe/Cu (atomic ratio)=1.00/1, Al/Cu (atomic ratio)=1.85/1, Zn/Cu (atomic ratio)=0.05/1), 25 parts by mass of polytitanocarbosilane "Tyranno Coat VN-100" (manufactured by Ube Industries, Ltd.) as a binder, and 60 parts by mass of methyl ethyl ketone were mixed together in a ball mill and thereby a coating material was obtained. The coating material was applied onto one side of a copper foil (40 μm in thickness and 15 cm×33 cm in width) (a support) with a bar coater. The catalyst layer coating material thus obtained on the copper foil was dried at 130° C. for one minute and then was heated in a nitrogen atmosphere at 250° C. for 90 minutes. Thus the binder contained in the coating material was cured. The catalyst layer coating material was applied onto the other side of the copper foil as in the above, and it was dried and heated as in the above. As a result, a film-type dehydrogenation catalyst with a 15-μm thick catalyst layer fixed to each side of the copper foil was obtained. The catalyst layer had a mass per unit area of 20.3 g/m² including the binder and the copper-based catalyst in the catalyst layer had a mass per unit area of 15.2 g/m².

Production Example 5

Production of Copper-Zinc Film-Type Catalyst 75 parts by mass of a copper/zinc catalyst "X213" (the composition ratio: Cu/Zn (atomic ratio)=1/0.9), 25 parts by mass of polytitanocarbosilane "Tyranno Coat VN-100" (manufactured by Ube Industries, Ltd.) as a binder, and 60 parts by mass of methyl ethyl ketone were mixed together in a ball mill and thereby a coating material was obtained. The coating material was applied onto one side of a copper foil (40 μm in thickness and 15 cm×33 cm in width) (a support) with a bar coater. The catalyst layer coating material thus obtained on the copper foil was dried at 130° C. for one minute and then was heated in a nitrogen atmosphere at 250° C. for 90 minutes. Thus the binder contained in the coating material was cured. The catalyst layer coating material was applied onto the other side of the copper foil as in the above, and it was dried and heated as in the above. As a result, a film-type dehydrogenation catalyst with a 15-μm thick catalyst layer fixed to each side of the copper foil was obtained. The catalyst layer had a mass per unit area of 27.6 g/m² including the binder and the copper-based catalyst in the catalyst layer had a mass per unit area of 20.7 g/m².

Example 1

Production of Octyl Aldehyde—Pellet-Type Catalyst—with Water

In Example 1, the reaction apparatus 10 shown in FIG. 1 was used. In the reaction apparatus 10, a plunger pump "LC-10AT" (manufactured by Shimadzu Corporation) was used for each of the raw material feed pump 12 and the water feed pump 25 and a mass flow controller "MC-10A" (model number, manufactured by KOFLOC) was used for the gas flow rate adjuster 22. Furthermore, a pipe made of SUS316 (with an inner diameter of 2.2 mm and a length of 800 mm) was used for the raw material preheating unit 13, the water preheating unit 26, and the gas preheating unit 23, a pipe made of SUS304 with a capacity of 92 mL (with an inner diameter of 28 mm and a pipe length of 150 mm) was used for the reaction unit 14, a double pipe cooler made of glass was used for the cooling unit 16, and a Wittmer fractionating receiver was used for the gas-liquid separation unit 17. A ribbon heater was used for the heating unit 15 for heating the raw material preheating unit 13, the water preheating unit 26, and the gas preheating unit 23 while a mantle heater was used for the heating unit 15 for heating the reaction unit 14. The double pipe cooler made of glass used for the cooling unit 16 was configured in such a manner that a reaction fluid flows through an inner pipe while tap water flows through an outer pipe. The raw material preheating unit 13, the gas preheating unit 23, and the water preheating unit 26 were connected to the inlet of the reaction unit 14 in parallel. The raw material preheating unit 13, the gas preheating unit 23, and the water preheating unit 26 were heated by the heating unit 15. The cooling unit 16 and the gas-liquid separation unit 17 were connected directly to the outlet of the reaction unit 14. The gas-liquid separation unit 17 carries out separation into a liquid product 18 and an exhaust gas 19. The reaction unit 14 was charged with 20.0 g of the pellet-type catalyst obtained in Production Example 1, as the dehydrogenation catalyst.

The raw material preheating unit 13, the gas preheating unit 23, and the water preheating unit 26 were heated to 250° C. for ten minutes using the heating unit 15. Octyl alcohol "KALCOL 0898" (manufactured by Kao Corporation), nitrogen, and water each were fed to the reaction unit 14. Octyl alcohol "KALCOL 0898" was fed at 0.41 g/min from the raw material alcohol feeder 11 through the raw material preheating unit 13 by the raw material feed pump 12. Nitrogen was fed at 646 mL/min from the gas feeder 21 through the gas preheating unit 23 by the gas flow rate adjuster 22. Water was fed at 0.006 g/min from the water feeder 24 through the water preheating unit 26 by the water feed pump 25. In this case, at the inlet of the reaction unit 14, the temperature of the reaction fluid was set at 250° C., the pressure thereof was set at normal pressure (101.3 kPa in absolute pressure, 10 kPa in partial pressure of the octyl alcohol, and 1 kPa (0.23 mol/m³) in partial pressure of the water), and the flow rate was set so that the retention time in the reaction unit 14 was 1.0 sec in terms of the inlet composition.

The point of time when the reaction temperature, the reaction pressure, and the respective feed flow rates reached set values is defined as the reaction initiation time. Thereafter, the internal temperature of the reaction unit 14 was increased to 250° C. by the heating unit 15. In this case, the reaction pressure was normal pressure (101.3 kPa in absolute pressure). The product produced inside the reaction unit 14 was condensed in the cooling unit 16 that had been cooled to 25° C. and was separated into a liquid product 18 and an exhaust gas 19 in the gas-liquid separation unit 17. The liquid product contained octyl aldehyde produced herein, unreacted alcohol, and other byproducts. The exhaust gas contained hydrogen and nitrogen. The liquid product that had been collected had a conversion rate of 60%. Furthermore, the selectivity was 94.5%. Moreover, the catalyst had a durability of –0.07%/h.

Comparative Example 1

Production of Octyl Aldehyde—Pellet-Type Catalyst—without Water

Comparative Example 1 was carried out in the same manner as in Example 1 except that water was not fed to the reaction unit 14 and thereby octyl aldehyde was obtained. The liquid product thus obtained had a conversion rate of 59%. Furthermore, the catalyst had a durability of –0.30%/h. The test conditions and results of Example 1 and Comparative Example 1 are shown together in Table 1.

TABLE 1

| | | | Example 1 | Comparative Example 1 |
|---|---|---|---|---|
| Test Conditions | Raw Material | | Octyl Alcohol | |
| | Catalyst Type | | Pellet-Type Catalyst | |
| | Catalyst | | Cu/Fe/Al | |
| | Reaction Temperature | ° C. | 250 | |
| | Reaction Pressure | kPa | Normal Pressure | |
| | Retention Time in Reaction Unit | sec | 1 | |
| | Alcohol Partial Pressure in Raw Material Gas | kPa | 10 | 10 |
| | Water Concentration in Raw Material Gas | mol/m³ | 0.23 | 0.02 |
| | Water Partial Pressure in Raw Material Gas | kPa | 1.0 | 0.1 |
| | Alcohol Flow Rate | g/min | 0.41 | 0.41 |
| | Water Flow Rate | g/min | 0.006 | 0 |
| | Nitrogen Flow Rate | mL/min | 646 | 646 |
| Result | Conversion Rate | % | 60 | 59 |
| | Durability | %/h | –0.07 | –0.30 |

Example 2

Octyl Aldehyde—Film Catalyst—with Water

Using the reaction apparatus 10 having the same configuration as that used in Example 1, the reaction unit 14 was charged with 3.3 g (in terms of a copper-based catalyst) of the film-type catalyst obtained in Production Example 3, as the dehydrogenation catalyst.

From the raw material feeder, the water feeder, and the gas feeder 21, 0.34 g/min of octyl alcohol "KALCOL 0898" (manufactured by Kao Corporation), 0.24 g/min of water, and 234 mL/min of nitrogen were fed, respectively. Then, at the inlet of the reaction unit 14, the temperature of the reaction fluid was set at 245° C., the pressure was set at normal pressure (101.3 kPa in absolute pressure, 10 kPa in partial pressure of the octyl alcohol, and 50 kPa in partial pressure of the water), and the flow rate was set so that the retention time in the reaction unit 14 was 5.0 sec in terms of the inlet composition. The reaction was carried out in the same manner as in Example 1 except for the changes described above. The liquid product collected herein had a conversion rate of 64%, a selectivity of 93.3%, and a catalyst durability of –0.02%/h. The evaluation results of the product obtained herein and the results of the catalyst durability are shown in Table 2.

Comparative Example 2

Octyl Aldehyde—Film Catalyst—without Water

Using the sample and the reaction apparatus 10 having the same configuration as that used in Example 2, 0.34 g/min of octyl alcohol and 535 mL/min of nitrogen were fed from the raw material feeder and the gas feeder, and a liquid product was collected from the liquid product collection pipe 34. The reaction was carried out in the same manner as in Example 1 except for the changes described above. The evaluation results of the product obtained herein and the results of the catalyst durability are shown in Table 2.

Example 3

Dodecyl Aldehyde—Film Catalyst—with Water

Using the reaction apparatus 10 having the same configuration as that used in Example 2, 0.48 g/min of lauryl alcohol "KALCOL 2098" (manufactured by Kao Corporation), 0.03 g/min of water, and 480 mL/min of nitrogen were fed from the raw material feeder, the water feeder, and the gas feeder 21, respectively. Then, at the inlet of the reaction unit 14, the temperature of the reaction fluid was set at 250° C., the pressure was set at normal pressure (101.3 kPa in absolute pressure, 10 kPa in partial pressure of the lauryl alcohol, and 7 kPa in partial pressure of the water), and the flow rate was set so that the retention time in the reaction unit 14 was 5.0 sec in terms of the inlet composition. The reaction was carried out in the same manner as in Example 1 except for the changes described above. The liquid product collected herein had a conversion rate of 67%, a selectivity of 96.8%, and a catalyst durability of –0.08%/h. The evaluation results of the product obtained herein and the results of the catalyst durability are shown in Table 2.

Example 4

Dodecyl Aldehyde—Film Catalyst—with Water

Using the reaction apparatus 10 having the same configuration as that used in Example 2, 0.48 g/min of lauryl alcohol "KALCOL 2098" (manufactured by Kao Corporation), 0.24 g/min of water, and 226 mL/min of nitrogen were fed from the raw material feeder, the water feeder, and the gas feeder 21, respectively. Then, at the inlet of the reaction unit 14, the temperature of the reaction fluid was set at 250° C., the pressure was set at normal pressure (101.3 kPa in absolute pressure, 10 kPa in partial pressure of the lauryl alcohol, and 51 kPa in partial pressure of the water), and the flow rate was set so that the retention time in the reaction unit 14 was 5.0 sec in terms of the inlet composition. The reaction was carried out in the same manner as in Example 1 except for the changes described above. The liquid product collected herein had a conversion rate of 62%, a selectivity of 95.0%, and a catalyst durability of −0.03%/h. The evaluation results of the product obtained herein and the results of the catalyst durability are shown in Table 2.

Example 5

Dodecyl Aldehyde—Film Catalyst—with Water

Using the reaction apparatus 10 having the same configuration as that used in Example 3, 0.48 g/min of lauryl alcohol "KALCOL 2098" (manufactured by Kao Corporation), 0.33 g/min of water, and 108 mL/min of nitrogen were fed from the raw material feeder, the water feeder, and the gas feeder 21, respectively. Then, at the inlet of the reaction unit 14, the temperature of the reaction fluid was set at 250° C., the pressure was set at normal pressure (101.3 kPa in absolute pressure, 10 kPa in partial pressure of the lauryl alcohol, and 71 kPa in partial pressure of the water), and the flow rate was set so that the retention time in the reaction unit 14 was 5.0 sec in terms of the inlet composition. The reaction was carried out in the same manner as in Example 1 except for the changes described above. The liquid product collected herein had a conversion rate of 62%, a selectivity of 93.1%, and a catalyst durability of −0.03%/h. The evaluation results of the product obtained herein and the results of the catalyst durability are shown in Table 2.

Example 6

Dodecyl Aldehyde—Film Catalyst—with Water

Using the reaction apparatus 10 having the same configuration as that used in Example 2, the reaction unit 14 was charged with 3.3 g (in terms of a copper-based catalyst) of the film-type catalyst obtained in Production Example 4, as the dehydrogenation catalyst.

From the raw material feeder, the water feeder, and the gas feeder 21, 0.47 g/min of lauryl alcohol "KALCOL 2098" (manufactured by Kao Corporation), 0.33 g/min of water, and 108 mL/min of nitrogen were fed, respectively. Then, at the inlet of the reaction unit 14, the temperature of the reaction fluid was set at 250° C., the pressure was set at normal pressure (101.3 kPa in absolute pressure, 10 kPa in partial pressure of the lauryl alcohol, and 50 kPa in partial pressure of the water), and the flow rate was set so that the retention time in the reaction unit 14 was 5.0 sec in terms of the inlet composition. The reaction was carried out in the same manner as in Example 1 except for the changes described above. The liquid product collected herein had a conversion rate of 65%, a selectivity of 92.0%, and a catalyst durability of −0.04%/h. The evaluation results of the product obtained herein and the results of the catalyst durability are shown in Table 2.

Example 7

Octyl Aldehyde—Film Catalyst—with Water

Using the reaction apparatus 10 having the same configuration as that used in Example 1, the reaction unit 14 was charged with 3.3 g (in terms of a copper-based catalyst) of the film-type catalyst obtained in Production Example 3, as the dehydrogenation catalyst.

From the raw material feeder, the water feeder, and the gas feeder 21, 0.34 g/min of octyl alcohol "KALCOL 0898" (manufactured by Kao Corporation), 0.01 g/min of water, and 526 mL/min of nitrogen were fed, respectively. Then, at the inlet of the reaction unit 14, the temperature of the reaction fluid was set at 220° C., the pressure was set at normal pressure (101.3 kPa in absolute pressure, 10 kPa in partial pressure of the octyl alcohol, and 2.2 kPa in partial pressure of the water), and the flow rate was set so that the retention time in the reaction unit 14 was 5.0 sec in terms of the inlet composition. The reaction was carried out in the same manner as in Example 1 except for the changes described above. The liquid product collected herein had a conversion rate of 47%, a selectivity of 97.0%, and a catalyst durability of −0.01%/h. The evaluation results of the product obtained herein and the results of the catalyst durability are shown in Table 2.

Comparative Example 3

Dodecyl Aldehyde—Film Catalyst—without Water

Using the sample and the reaction apparatus 10 having the same configuration as that used in Example 6, 0.47 g/min of lauryl alcohol and 521 mL/min of nitrogen were fed from the raw material feeder and the gas feeder, and a liquid product was collected from the liquid product collection pipe 35. The reaction was carried out in the same manner as in Example 1 except for the changes described above. The evaluation results of the product obtained herein and the results of the catalyst durability are shown in Table 2.

Comparative Example 4

Octyl Aldehyde—Copper/Zinc Film Catalyst—with Water

Using the reaction apparatus 10 having the same configuration as that used in Example 2, the reaction unit 14 was charged with 2.7 g (in terms of a copper-based catalyst) of the film-type catalyst obtained in Production Example 5, as the dehydrogenation catalyst.

From the raw material feeder, the water feeder, and the gas feeder 21, 0.34 g/min of octyl alcohol "KALCOL 0898" (manufactured by Kao Corporation), 0.005 g/min of water, and 535 mL/min of nitrogen were fed, respectively. Then, at the inlet of the reaction unit 14, the temperature of the reaction fluid was set at 240° C., the pressure was set at normal pressure (101.3 kPa in absolute pressure, 10 kPa in partial pressure of the octyl alcohol, and 1 kPa in partial pressure of the water), and the flow rate was set so that the retention time in the reaction unit 14 was 5.0 sec in terms of the inlet composition. The reaction was carried out in the same manner as in Example 1 except for the changes described above. The evaluation results of the product obtained herein and the results of the catalyst durability are shown in Table 2.

Comparative Example 5

Octyl Aldehyde—Copper/Zinc Film Catalyst—with Water

Using the reaction apparatus 10 having the same configuration as that used in Comparative Example 4, 0.34 g/min of octyl alcohol "KALCOL 0898" (manufactured by Kao Corporation), 0.034 g/min of water, and 535 mL/min of nitrogen were fed from the raw material feeder, the water feeder, and the gas feeder 21, respectively. Then, at the inlet of the reaction unit 14, the temperature of the reaction fluid was set at 240° C., the pressure was set at normal pressure (101.3 kPa in absolute pressure, 9 kPa in partial pressure of the octyl alcohol, and 7 kPa in partial pressure of the water), and the flow rate was set so that the retention time in the reaction unit 14 was 5.0 sec in terms of the inlet composition. The reaction was carried out in the same manner as in Example 1 except for the changes described above. The evaluation results of the product obtained herein and the results of the catalyst durability are shown in Table 2.

The test conditions and results of Examples 2 to 6 and Comparative Examples 2 to 5 are shown together in Table 2.

18 Liquid Product
19 Exhaust Gas
21 Gas Feeder
22 Gas Flow Rate Adjuster
23 Gas Preheating Unit
24 Water Feeder
25 Water Feed Pump
26 Water Preheating Unit
31 Raw Material Alcohol Feed Pipe

TABLE 2

| | | | Ex. 2 | C. Ex. 2 | Ex. 3 | Ex. 4 | Ex. 5 | Ex. 6 | Ex. 7 | C. Ex. 3 | C. Ex. 4 | C. Ex. 5 |
|---|---|---|---|---|---|---|---|---|---|---|---|---|
| Test Conditions | Raw Material | | Octyl Alcohol | Octyl Alcohol | Lauryl Alcohol | Lauryl Alcohol | Lauryl Alcohol | Lauryl Alcohol | Octyl Alcohol | Lauryl Alcohol | Octyl Alcohol | Octyl Alcohol |
| | Catalyst Type | | Film-Type Catalyst | Film-Type Catalyst | Film-Type Catalyst | Film-Type Catalyst | Film-Type Catalyst | Film-Type Catalyst | Film-Type Catalyst | Film-Type Catalyst | Film-Type Catalyst | Film-Type Catalyst |
| | Catalyst | | Cu/Fe/Al | Cu/Fe/Al | Cu/Fe/Al | Cu/Fe/Al | Cu/Fe/Al | Cu/Fe/Al/Zn | Cu/Fe/Al | Cu/Fe/Al/Zn | Cu/Zn | Cu/Zn |
| | Reaction Temperature | °C. | 245 | 245 | 250 | 250 | 250 | 250 | 220 | 250 | 240 | 240 |
| | Retention Time in Reaction Unit | sec | 5 | 5 | 5 | 5 | 5 | 5 | 5 | 5 | 5 | 5 |
| | Alcohol Partial Pressure in Raw Material Gas | kPa | 10 | 10 | 10 | 10 | 10 | 10 | 10 | 10 | 10 | 9 |
| | Water Concentration in Raw Material Gas | mol/m³ | 11.6 | 0.02 | 1.6 | 11.7 | 16.3 | 16.3 | 0.53 | 0.02 | 0.23 | 1.6 |
| | Water Partial Pressure in Raw Material Gas | kPa | 50 | 0.1 | 7 | 51 | 71 | 71 | 2.2 | 0.1 | 1 | 7 |
| | Alcohol Flow Rate | g/min | 0.34 | 0.34 | 0.48 | 0.48 | 0.48 | 0.47 | 0.34 | 0.47 | 0.34 | 0.34 |
| | Water Flow Rate | g/min | 0.24 | 0 | 0.03 | 0.24 | 0.33 | 0.33 | 0.01 | 0 | 0.005 | 0.034 |
| | Nitrogen Flow Rate | mL/min | 234 | 535 | 480 | 226 | 108 | 108 | 526 | 521 | 535 | 535 |
| Result | Conversion Rate | % | 64 | 60 | 67 | 62 | 62 | 65 | 47 | 66 | 57.2 | 54.1 |
| | Durability | %/h | −0.02 | −0.41 | −0.08 | −0.03 | −0.03 | −0.04 | −0.01 | −0.92 | −0.11 | −0.69 |

With reference to Tables 1 and 2, it was confirmed that the production methods of the examples allowed the target aldehyde to be obtained at high conversion rates over an extended period of time as compared to the production methods of the comparative examples.

INDUSTRIAL APPLICABILITY

Since the production methods of the present invention provides the target aldehyde at high conversion rates over an extended period of time, particularly a primary aldehyde can be produced efficiently. Such production methods can be used suitably as methods for producing an aldehyde that is useful as a fragrance material.

DESCRIPTION OF THE NUMERALS

10 Reaction Apparatus
11 Raw Material Alcohol Feeder
12 Raw Material Feed Pump
13 Raw Material Preheating Unit
14 Reaction Unit
15 Heating Unit
16 Cooling Unit
17 Gas-Liquid Separation Unit
32 Gas Feed Pipe
33 Water Feed Pipe
34 Product Collection Pipe
35 Liquid Product Collection Pipe
36 Exhaust Gas Discharge Pipe

The invention claimed is:

1. A method for producing an aldehyde comprising bringing a raw material gas containing a primary alcohol having 4 to 18 carbon atoms and water into contact with a dehydrogenation catalyst containing copper and iron so as to dehydrogenate the alcohol contained in the raw material gas, thereby obtaining an aldehyde,
  wherein the raw material gas has a water partial pressure of 0.2 kPa to 99 kPa.

2. The method for producing the aldehyde according to claim 1, wherein the raw material gas has a water partial pressure of 1 kPa to 90.

3. The method for producing the aldehyde according to claim 1, wherein the raw material gas has a water partial pressure of 10 kPa to 80 kPa.

4. The method for producing the aldehyde according to claim 1, wherein the raw material gas has a water partial pressure of 40 kPa to 80 kPa.

5. The method for producing the aldehyde according to claim 1, wherein the water concentration in the reaction raw material gas is at least 0.05 mol/m$^3$ and not more than 23 mol/m$^3$.

6. The method for producing the aldehyde according to claim 1, wherein the water concentration in the reaction raw material gas is at least 0.11 mol/m$^3$ and not more than 20 mol/m$^3$.

7. The method for producing the aldehyde according to claim 1, wherein the water concentration in the reaction raw material gas is at least 0.40 mol/m$^3$ and not more than 18 mol/m$^3$.

8. The method for producing the aldehyde according to claim 1, wherein the primary alcohol has 6 to 15 carbon atoms.

9. The method for producing the aldehyde according to claim 1, wherein the primary alcohol has 8 to 15 carbon atoms.

10. The method for producing the aldehyde according to claim 1, wherein the primary alcohol has 8 to 12 carbon atoms.

11. The method for producing the aldehyde according to claim 1, wherein the dehydrogenation catalyst further comprises a metal element in addition to copper and iron.

12. The method for producing the aldehyde according to claim 11, wherein the metal element in addition to copper and iron is at least one selected from the group consisting of zinc, chromium, cobalt, nickel, manganese, aluminum, silicic acid, and titanium.

13. The method for preparing the aldehyde according to claim 11, wherein the metal element in addition to copper and iron is zinc and aluminum.

14. The method for producing the aldehyde according to claim 1, wherein a reaction temperature is 200° C. to 300° C.

15. The method for producing the aldehyde according to claim 1, wherein a reaction pressure is not more than 102 kPa in absolute pressure.

16. The method for producing the aldehyde according to claim 1, wherein the primary alcohol of the raw material gas has a partial pressure of 1 kPa to 50 kPa.

17. The method for producing the aldehyde according to claim 1, wherein the dehydrogenation catalyst is a pellet-type catalyst.

18. The method for producing the aldehyde according to claim 1, wherein the dehydrogenation catalyst is a film-type catalyst.

19. The method for producing the aldehyde according to claim 1, wherein the step for bringing the gas into contact with the dehydrogenation catalyst is carried out by continuously passing the gas through a reactor charged with the dehydrogenation catalyst.

20. The method for producing the aldehyde according to claim 1, wherein the reactor that is used for the dehydrogenation step is a tubular flow reactor.

* * * * *